US009311686B2

(12) United States Patent
Roush et al.

(10) Patent No.: US 9,311,686 B2
(45) Date of Patent: Apr. 12, 2016

(54) FITNESS MONITOR (71) Applicant: Garmin Switzerland GmbH, Schaffhausen (CH)

(72) Inventors: Adam W. Roush, Prairie Village, KS (US); Robert M. Kalis, Overland Park, KS (US)

(73) Assignee: Garmin Switzerland GmbH (CH)

( * ) Notice: Subject to any disclaimer, the term of this patent is extended or adjusted under 35 U.S.C. 154(b) by 150 days.

(21) Appl. No.: 14/147,284

(22) Filed: Jan. 3, 2014

(65) Prior Publication Data

US 2015/0105221 A1 Apr. 16, 2015

Related U.S. Application Data (60) Provisional application No. 61/890,636, filed on Oct. 14, 2013.

(51) Int. Cl.
| *A63B 24/00* | (2006.01) |
| *G06Q 50/22* | (2012.01) |
| *A61B 5/024* | (2006.01) |
| *A61B 5/11* | (2006.01) |
| *G06Q 10/06* | (2012.01) |
| *A61B 5/00* | (2006.01) |

(52) U.S. Cl.
CPC ............ *G06Q 50/22* (2013.01); *A61B 5/02405* (2013.01); *A61B 5/02438* (2013.01); *A61B 5/1118* (2013.01); *A61B 5/7278* (2013.01); *G06Q 10/0639* (2013.01); *A61B 5/681* (2013.01)

(58) Field of Classification Search
CPC ... A63B 24/00; G06Q 50/22; G06Q 10/0639; A61B 5/02405; A61B 5/02438; A61B 5/1118; A61B 5/681; A61B 5/7278

IPC ......................................................... A63B 24/00
See application file for complete search history.

(56) References Cited

U.S. PATENT DOCUMENTS

| 7,793,361 | B2 * | 9/2010 | Ishihara et al. ................... 2/170 |
| 8,345,412 | B2 * | 1/2013 | Maravilla et al. ......... 361/679.03 |
| 8,534,514 | B2 * | 9/2013 | Zhu et al. ...................... 224/165 |
| 9,028,405 | B2 * | 5/2015 | Tran ............................. 600/300 |
| 2005/0177051 | A1 | 8/2005 | Almen ........................... 600/509 |
| 2007/0194066 | A1 * | 8/2007 | Ishihara et al. ............... 224/164 |

(Continued)

OTHER PUBLICATIONS

Printout from http://designshack.net/design/nike-sport-band; published prior to Jan. 3, 2014.

(Continued)

*Primary Examiner* — Glenn Richman
(74) *Attorney, Agent, or Firm* — Samuel M. Korte; Max M. Ali (57) ABSTRACT

A fitness monitor having a unitary wristband configured to receive a module, such as an electronics module, is disclosed. In one or more implementations, the fitness monitor comprises a module, such as an electronics module, that includes a housing having a first thickness. The fitness monitor also comprises a unitary wristband configured to be worn about a wrist of a user. The unitary wristband includes a housing receiving structure configured to receive the housing of the module so that the combination of the housing receiving structure and the housing has a second thickness, where the second thickness is at least substantially equal to the first thickness. In embodiments, the housing of the monitor may further have a first width, and the combination of the housing receiving structure and the housing may have a second width, where the second width is at least substantially equal to the first width.

23 Claims, 5 Drawing Sheets

(56) References Cited

U.S. PATENT DOCUMENTS

| | | | |
|---|---|---|---|
| 2007/0276270 A1 | 11/2007 | Tran | 600/508 |
| 2008/0074958 A1* | 3/2008 | Moran | 368/282 |
| 2009/0138636 A1 | 5/2009 | Burton et al. | 710/63 |
| 2009/0196124 A1 | 8/2009 | Mooring | 368/204 |
| 2009/0280861 A1* | 11/2009 | Khan | 455/556.1 |
| 2010/0292050 A1 | 11/2010 | DiBenedetto et al. | 482/9 |
| 2012/0087216 A1* | 4/2012 | Keung et al. | 368/282 |
| 2012/0277014 A1* | 11/2012 | Caldwell | 473/213 |

OTHER PUBLICATIONS

Printout from http://mashable.com/2013/07/02/fitbit-flex-review; published prior to Jan. 3, 2014.

Printout from http://www.dcrainmaker.com/2012/08/nike-fuelband-in-depth-review.html; published prior to Jan. 3, 2014.

International Search Report and Written Opinion from corresponding PCT Application No. PCT/US2014/032541 dated Aug. 21, 2014.

* cited by examiner

FITNESS MONITOR

CROSS-REFERENCE TO RELATED APPLICATIONS

The present application claims the benefit under 35 U.S.C. §119(e) of U.S. Provisional Application Ser. No. 61/890,636, entitled FITNESS MONITOR, filed on Oct. 14, 2013. U.S. Provisional Application Ser. No. 61/890,636 is herein incorporated by reference in its entirety.

BACKGROUND

A fitness monitor is an electronic device that tracks the activity of a user, typically by sensing the motion of the user such as by determining the number of steps taken by the user. A fitness monitor, such as the Garmin VivoFit wellness product, may be worn by a user to monitor (e.g., measure or sense) the user's physical activity and receive information associated with the physical activity from the wellness product, such as a heart monitor, or the like. Some fitness monitors may be worn on a user's wrist, arm, torso, leg, etc. Other fitness monitors may be carried or attached to clothing. Some fitness monitors include additional features such as clock displays for presenting the time of day, communication modules for communicating wirelessly with other electronic devices, and so forth.

SUMMARY

A fitness monitor having a unitary wristband configured to receive a module, such as an electronics module, is disclosed. In one or more implementations, the fitness monitor comprises a module, such as an electronics module, that includes a housing having a first thickness. The fitness monitor also comprises a unitary wristband configured to be worn about a wrist of a user. The unitary wristband includes a housing receiving structure configured to receive the housing of the module so that the combination of the housing receiving structure and the housing has a second thickness, where the second thickness is at least substantially equal to the first thickness. In embodiments, the housing of the monitor may further have a first width, and the combination of the housing receiving structure and the housing may have a second width, where the second width is at least substantially equal to the first width.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different instances in the description and the figures may indicate similar or identical items.

DETAILED DESCRIPTION

Overview

Conventional fitness monitors include wristbands that fully enclose the top and sides of the housing of the electronics module when the monitors are worn on a user's wrist. The conventional fitness monitors require inserting the housing into a cavity within the wristband that prevents the housing from being visible when the conventional fitness monitor is worn (e.g., the top and sides of the housing are covered). Consequently, the conventional configuration requires use of a wristband that is wider (e.g., the length of user's wrist that is covered by the fitness monitor is greater) and thicker (e.g., the height of the fitness monitor above the user's wrist is greater) than the enclosed housing.

Implementations of the present disclosure provide a fitness monitor for tracking the activity levels of a user that includes a wristband that does not fully cover the top and/or one or more sides of the housing. For example, a wristband may cover the housing in such a manner that a portion of the top of the housing, which may include a display, is exposed. Exposing the top of the housing facilitates the use of a wristband that is not thicker than the housing of the module. Similarly, a wristband may cover the housing in such a manner that at least a portion of one or more sides of the housing extending along the length of the wristband are exposed. Exposing the sides extending along the length of the wristband facilitates the use of a wristband that is not wider than the housing of the module. Thus, fitness monitors in accordance with implementations of the present disclosure employ a unitary wristband that exposes portions of a top surface and side surfaces of the housing of the electronics module so that the wristband is neither thicker nor wider than the housing.

In one or more implementations, the fitness monitor comprises a module, such as an electronics module, that includes a housing having a first thickness. The fitness monitor also comprises a unitary wristband configured to be worn about a wrist of a user to secure the module to the wrist of the user. The unitary wristband includes a housing receiving structure configured to receive the housing of the module, so that the combination of the housing receiving structure and the housing has a second thickness. In implementations, the second thickness is at least substantially equal to the first thickness.

In embodiments, the module comprises an electronics module having a display, a non-transitory memory device, a battery, and a processor. The display of the module may be part of, or coupled to, the housing and configured to present (e.g., display) information associated with the user's activities, such as a daily activity goal and activity data of the user. The memory device is located in the housing and configured to store the user's activity information, including the daily activity goal and the activity data. The processor is included in the housing and operably coupled to the memory device and display. The battery may be received in the housing and provides power to electrical components in the housing. The housing may include a lens that is positioned above the display to protect the display from debris and impact. The lens may be composed of one or more layers of transparent material to maintain the visibility of content presented on the display.

The fitness monitor generally tracks the activity levels of a user in order to promote good health and fitness. The processor of the fitness monitor may determine, based on daily activity data, a daily activity goal corresponding to a predetermined level of activity for the user in a day, compute a level of inactivity corresponding to a mathematical difference between a current activity associated with the user in a first time period and a predetermined inactivity value. The fitness monitor display may present information associated with any physical activity. For example, a motion sensor of fitness monitor may sense motion of the user wearing the fitness monitor associated with swimming (e.g., number of strokes, length of strokes, etc.), skating (e.g., ice skating, inline skating, etc.), skiing, rowing, bicycling, aerobics, or any other physical activity. The fitness monitor may determine a heart rate for a user and determine user activity based on heart rate information. In embodiments, a communication port may receive data associated with a user's heart rate. The heart rate data may be received by the processor to determine user activity, an activity count down toward reaching a daily activity goal, and a number of calories burned. The display may be configured to present user activity information determined based on heart rate information associated with the user, motion sensed by the motion sensor, or a combination thereof. The processor may also use the heart rate information to determine heart rate variability. The fitness monitor may determine energy expenditure based on heart rate information, such as heart rate variability, and user-specific information, such as age, gender, weight, height and fitness class (i.e., overall physical fitness level).

Example Fitness Monitor

FIGS. 1 through 8 generally illustrate a fitness monitor 100 in accordance with one or more example implementations of the present disclosure. As shown, the fitness monitor 100 includes a module 101 that comprises a housing 102 which at least partially encloses components of the module 101. For example, in embodiments, the module 101 may comprise an electronics module that includes components such as a display 106, a user interface 108, a communication port 110, a motion sensor 112, a non-transitory memory device 114, a processor 116, a battery 118, and so forth. The housing 102 is received in and coupled to a unitary (e.g., continuous) wristband 104.

Figure 2:
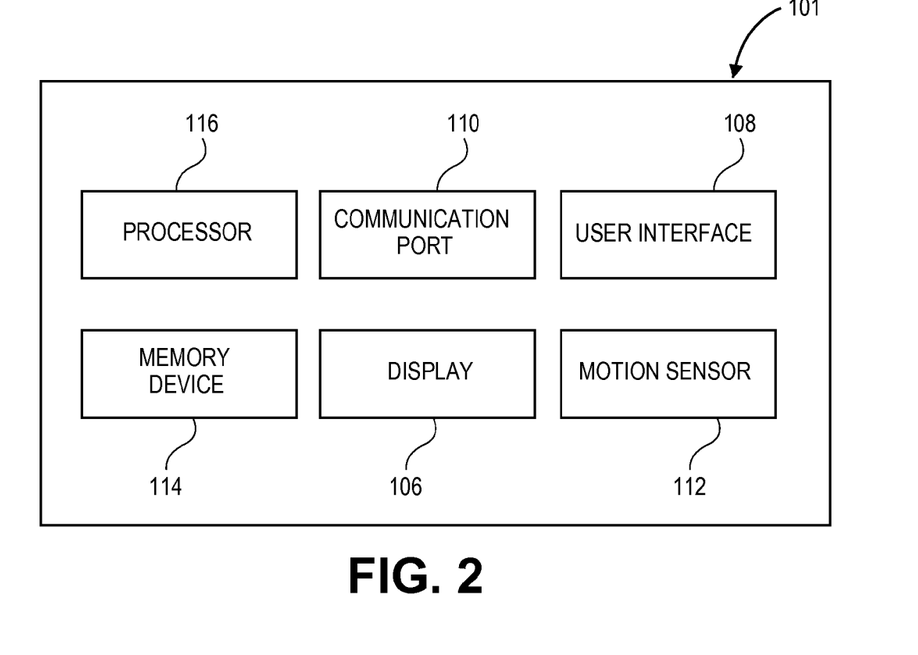
FIG. 2 is a block diagram illustrating the various components of the electronics module of an example fitness monitor such as the fitness monitor depicted in FIG. 1.

The display 106 generally presents information associated with the user's activity. For example, the display 106 may present the user's daily activity goals and activity data. The display 106 may be formed from, or may include, the following technologies: light-emitting diode (LED), organic LED (OLED), Light Emitting Polymer (LEP) or Polymer LED (PLED), liquid crystal display (LCD), thin film transistor (TFT) LCD, plasma, electronic paper, electronic ink, combinations thereof, and so forth. The display 106 may be coupled to an upper or outer surface of the housing 102 and may receive information to be presented from the processor 116.

The user interface 108 generally allows the user to select the information that is displayed by the display 106, and may include one or more pushbuttons, or touch areas, such as a touchscreen, or the like. For example, the user may activate the user interface 108 (e.g., by pushing a button) to cycle through a plurality of screens of data, wherein each screen of data may include informational items, such as those described herein. In embodiments, the user interface 108 may be located either on the housing 102, on the display 106, or on the wrist band 104.

The communication port 110 generally allows the user to upload data to, download data from, or adjust the settings of the fitness monitor 100. The communication port 110 may be wired or wireless and may include antennas, signal or data receiving circuits, and signal or data transmitting circuits. The communication port 110 may transmit and receive radio frequency (RF) signals and/or data and may operate utilizing communication standards such as ANT, ANT+, Bluetooth™ low energy (BLE), Near Field Communications (NFC), or the like. In various implementations, the communication port 110 may transmit and receive data using the industrial, scientific, and medical (ISM) band at 2.4 gigahertz (GHz). Furthermore, in some implementations, the communication port 110 may communicate with a wireless dongle that connects to the USB port of a desktop, laptop, notebook, or tablet computer, or other electronic device. In a specific implementation, the communication port 110 includes an nRF519112 RF integrated circuit (IC).

The fitness monitor 100 may furnish an input/output interface that may enable interaction between the fitness monitor 100 and an external display, processor, memory device, and/or user interface associated with a secondary electronic device (e.g., associated with a smartphone, tablet, personal computer, etc.). In implementations, an external display and user interface may be utilized by the fitness monitor 100 to present fitness information provide and provide user interface functionality. Thus, in an embodiment, the fitness device 100 may not include the display 106 and may utilize an external display to present fitness information and provide user interface functionality. In other embodiments, the fitness device 100 may supplement the functionality of the display 106 and user interface included in the fitness device 100 with an external display, processor, memory device and/or user interface associated with the secondary electronic device. For example, the fitness device 100 may utilize the communication port 110 to transmit fitness data (unprocessed, semi-processed or fully processed) to enable a secondary electronic device to provide user interface and/or visual or audible output functionality (using a display or speaker associated with the secondary device), processing functionality (using a processor associated with the secondary device) or data storage functionality (using a memory device associated with the secondary device). In implementations, external components may be operable to perform any of the functionality associated with the display 106, the user interface 108, the memory device 114, the motion sensor 112 or the processor 116 as described herein.

The motion sensor 112 generally senses motion of the fitness monitor 100 and, in turn, the user wearing the fitness monitor 100 on a limb (e.g., wrist, arm, torso, leg, ankle, etc.) carrying the fitness monitor 100 or having the fitness monitor 100 attached to clothing or accessories commonly stored on the user's body (e.g., keys, workplace security badge, etc.). The motion sensor 112 may include accelerometers, tilt sensors, inclinometers, gyroscopes, combinations thereof, or other devices including piezoelectric, piezoresistive, capacitive sensing, or micro electromechanical systems (MEMS) components. The motion sensor 112 may sense motion along one axis of motion or multiple axes of motion, such as the three orthogonal axes X, Y, and Z. In a specific implementation, the motion sensor 112 comprises an ADXL362 3-axis accelerometer from Analog Devices of Norwood, Mass. The motion sensor 112 generally communicates motion data to the processor 116. The rate at which the motion sensor 112 communicates motion data may vary from approximately fifty hertz (50 Hz) to approximately one hundred hertz (100 Hz).

The memory device 114 generally stores information regarding daily activity goals and activity data and may include non-transitory components such as read-only memory (ROM), programmable ROM, erasable programmable ROM, random-access memory (RAM), cache memory, and the like, or combinations thereof. The memory device 114 may store instructions, code, code segments, software, firmware, programs, applications, apps, services, daemons, or the like. In embodiments of the fitness monitor 100, the memory device 114 may include removable ICC (Integrated Circuit Card) memory such as provided by SIM (Subscriber Identity Module) cards, USIM (Universal Subscriber Identity Module) cards, UICC (Universal Integrated Circuit Cards), and so on.

The processor 116 generally determines levels of inactivity and whether daily activity goals are met. The processor 116 may also be configured to determine a user's activity data based upon the motion data generated by the motion sensor 112. The processor 116 may include processors, microprocessors, microcontrollers, digital signal processors (DSPs), field-programmable gate arrays (FPGAs), analog and/or digital application-specific integrated circuits (ASICs), or the like, or combinations thereof. In a specific implementation, the processor 116 comprises a 32-bit Cortex M0 processor, licensed by ARM Holdings of Cambridge, England. In various implementations, the Cortex M0 processor is packaged with the nRF519112 RFIC of the communication port 110. The processor 116 may further include or be in communication with oscillators or periodic signal generators from which the time of day can be derived. The processor 116 may generally execute, process, or run instructions, code, code segments, software, firmware, programs, applications, apps, processes, services, daemons, or the like, or may step through states of a finite-state machine. The processor 116 may be in communication with the memory device 114 through address busses, data busses, control lines, and the like. Furthermore, the processor 116 may send data to the display 106, may receive data from the motion sensor 112 and the user interface 108, and may send and receive data from the communication port 110.

In implementations, the module 101 may include a location determining component to determine a current location of the monitor 100. The location determining component may include a global positioning system (GPS) receiver, a satellite navigation receiver (e.g., GLONASS), a cellular signal receiver, an RF triangulation processor, an enhanced positioning system such as real time kinematic (RTK), or combinations thereof. The location determining component may supply the current location of the housing 102 to the processor 116.

Figure 1:
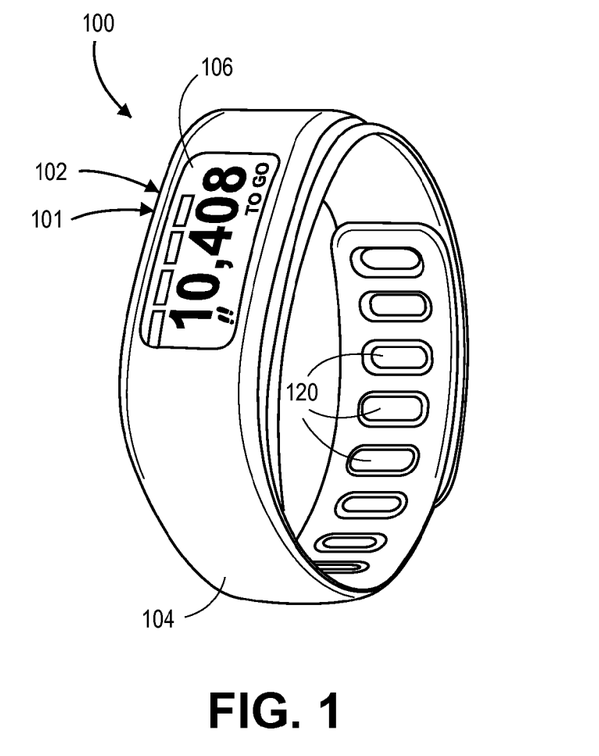
FIG. 1 is a perspective view illustrating a fitness monitor in accordance with an example implementation of the present disclosure.

The thickness of the fitness monitor 100 may be influenced by the dimensions of its components, such as the height of the housing 102 of the module 101 and the unitary wristband 104. The wristband 104, as seen in FIG. 1, generally allows the fitness monitor 100 to be worn on the wrist of the user. When the wristband 104 is worn on a user's wrist, the fitness monitor 100 may resemble a wristwatch. However, in implementations, the wristband 104 may be modified to allow the fitness monitor 100 to be worn (secured to) other parts of the user's body (e.g., arm, torso, leg, ankle, etc.) or to the user's clothing (e.g., shirt, belt, shoe, etc.) as a clip.

The unitary wristband 104 may enhance the appearance and comfort of a fitness device. In embodiments, the wristband 104 may be formed from flexible (e.g., supple and/or elastic) material such that the fitness monitor 100 can be worn by the user for long periods of time. The wristband 104 may include a plurality of holes 120 and one or more corresponding coupling mechanisms 122 that allow the length of the wristband 104 to be adjusted. The wristband 104 may couple to opposing ends of the housing 102.

Figure 3:
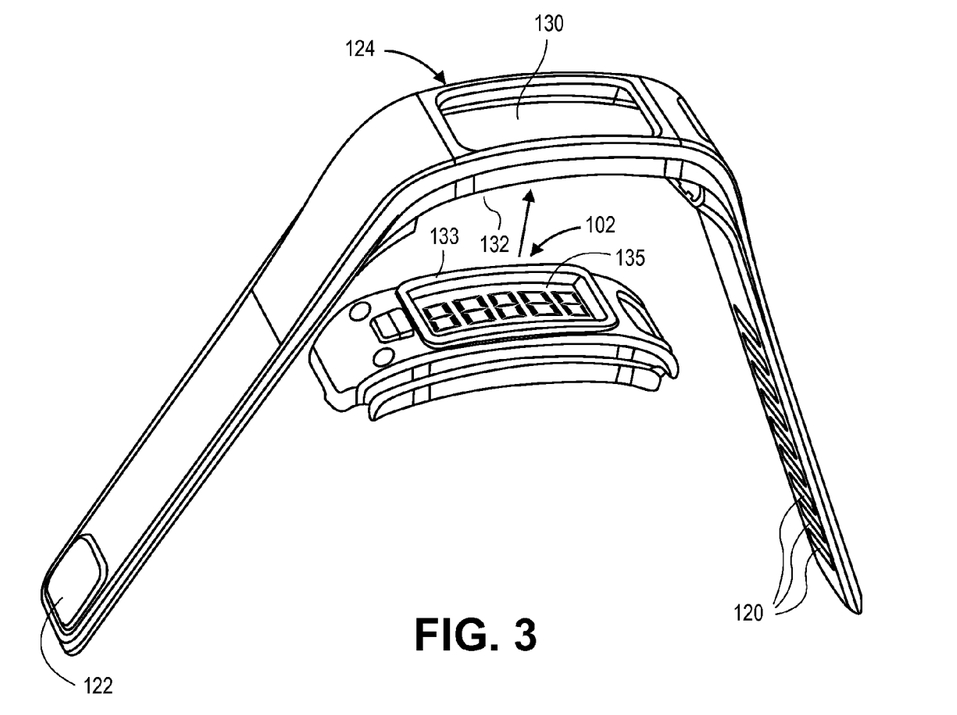
FIG. 3 is a perspective exploded view of the fitness monitor depicted in FIG. 1, further illustrating the electronics module and unitary wristband of the fitness monitor.
Figure 4:
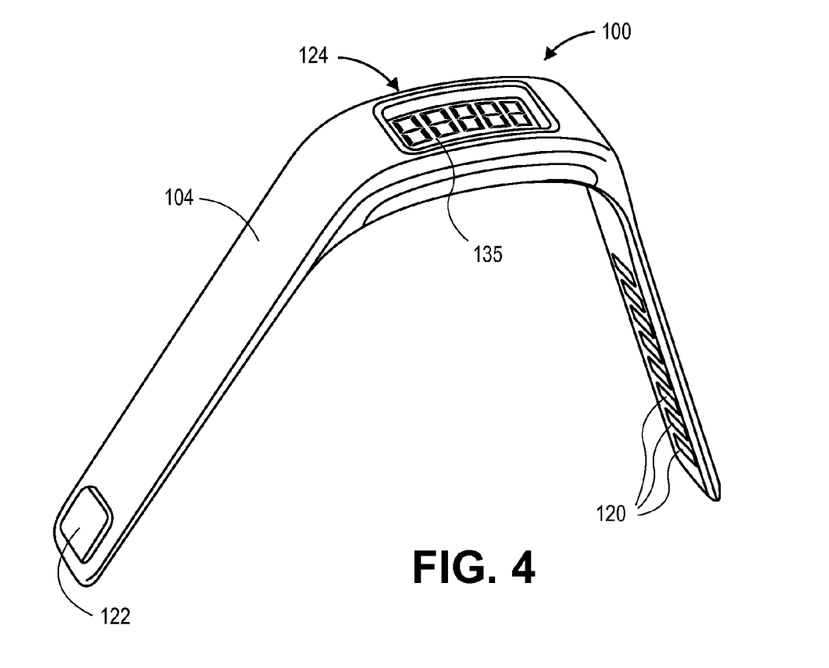
FIG. 4 is a perspective view illustrating the fitness monitor depicted in FIG. 1, wherein the unitary wrist band is shown in an unfastened orientation.

As shown in FIGS. 3 and 4, the unitary wristband 104 may have a substantially continuous form, and may include a housing receiving structure 124 integrated within the wristband 104. In embodiments, the housing receiving structure 124 may be an inseparable part of the unitary wristband 104 such that the combination forms a single wristband 104 that is worn about a wrist of a user and receives housing 102 to form a wrist-worn fitness monitor 100 (i.e., the housing 102 may be inserted into the housing receiving structure 124 integrated within wristband 104 such that the housing 102 and wristband 104 are secured together to form a wrist-worn fitness monitor 100).

The housing receiving structure 124 is configured to receive and secure the housing 102 of the monitor 101, which is described in greater detail below. The housing 102 may include the display 106, and may be received in the housing receiving structure so that the display 106 faces away from the user's wrist when the fitness monitor 100 is worn. In one or more implementations of the present disclosure, the thickness of the combination of the housing 102 and the housing receiving structure 124 is at least substantially the same thickness as the housing 102. Similarly, in some implementations, the width of the combination of the housing 102 and the housing receiving structure 124 is at least substantially the same width as the housing 102.

Unlike conventional fitness monitors that couple two wristbands with a housing (e.g., two wristbands attached to opposite side surfaces of a housing), implementations of the present disclosure utilize a single, unitary wristband 104 having a housing receiving structure 124 in which the housing 102 of the module 101 may be received and secured. The unitary wristband 104 may be a single-body element that wraps around a user's wrist. Thus, unlike conventional wrist-worn devices having two bands, the wristband 104 of the present disclosure may have a continuous form. In embodiments, as shown in FIGS. 1, 3, 4, and 7, the wristband 104 may be formed of a unitary material from one end to the other without interruption or gaps.

Figure 5:
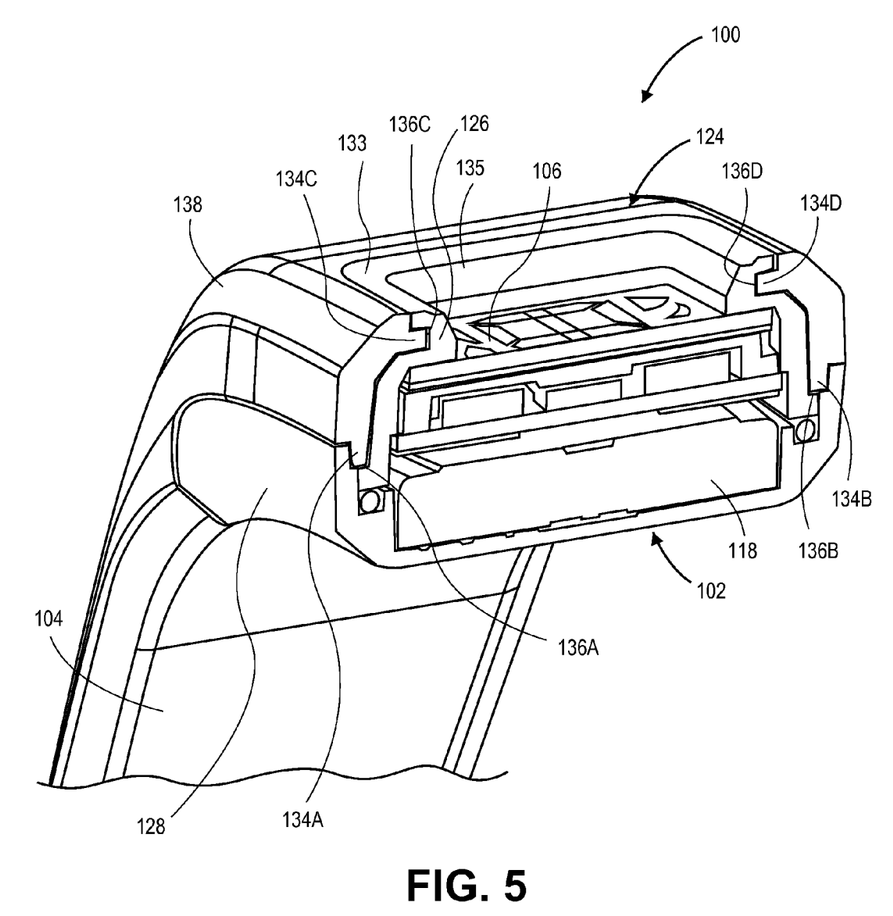
FIG. 5 is a cross-sectional illustration of the fitness monitor depicted in FIG. 1.
Figure 6:
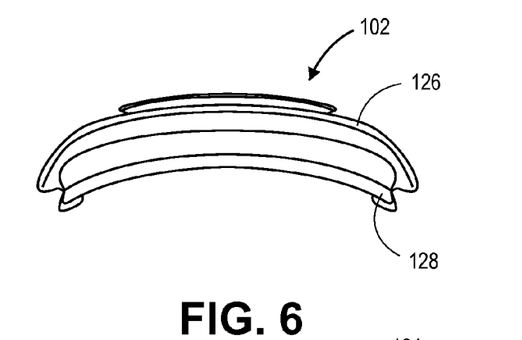
FIG. 6 is a side elevation view illustrating the housing of the electronics module of the fitness monitor shown in FIG. 1, in accordance with an example implementation of the present disclosure.

As shown in FIGS. 5 and 6, the housing 102 of the module 101 may include an upper portion 126 and a lower portion 128 that may be secured together using a plurality of fasteners, such as screws, or the like. The upper portion 126 comprises the portion of the housing 102 that is distal to the user's wrist, while the lower portion 128 comprises the portion of the housing 102 that is proximal to the user's wrist. The housing 102 may be positioned within the housing receiving structure 124 in a manner that conceals the one or more fasteners (e.g., screws) which secure the upper and lower portions 126, 128 of the housing 102 together. Removal of the fasteners may enable access (e.g., by the user, a service technician, or the like) to an inner chamber of the housing 102 to service or replace components contained therein. For example, four screws may be used to secure the upper portion 126 and the lower portion 128 of the wristband 104. Removal of the screws may enable a user to replace one or more batteries 118 (e.g., two 1632 coin cell batteries) stored therein. In implementations having two or more batteries 118, the batteries 118 may be stored next to each other rather than using a stacked arrangement to minimize the height of the housing 102. In some implementations, a seal may be furnished between the upper portion 126 and the lower portion 128 of the housing 102 so that the housing 102 is environmentally resistant (e.g., water resistant, water proof, etc.). For example, in an embodiment, the housing 102 may be waterproof up to fifty (50) meters of water depth.

Figure 7:
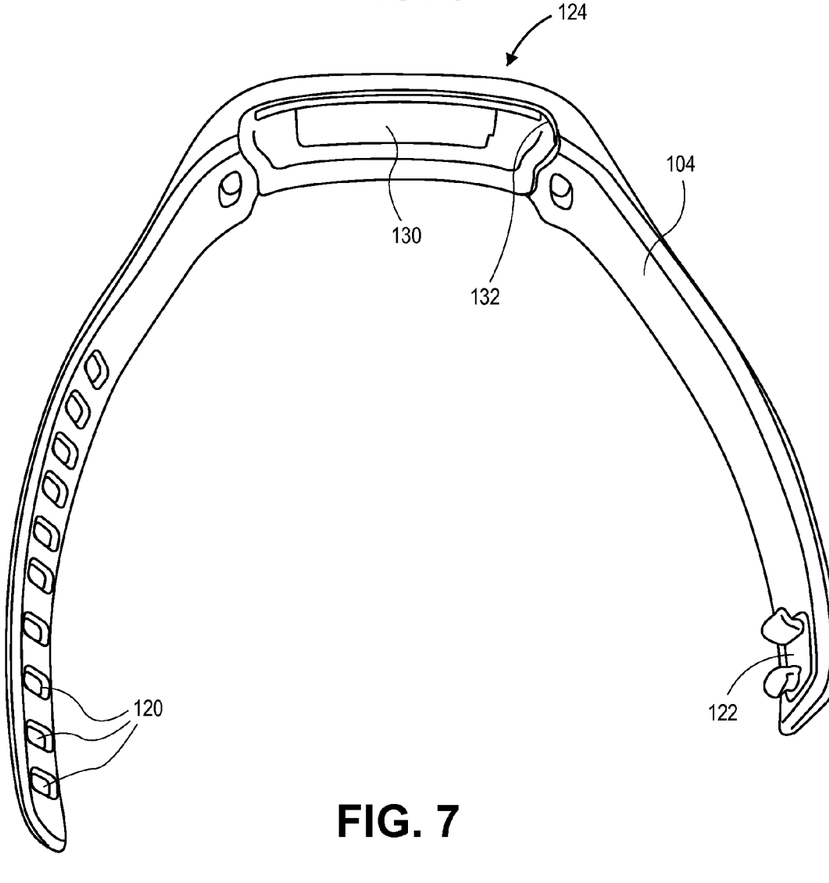
FIG. 7 is a perspective view illustrating the unitary wristband of the fitness monitor shown in FIG. 1, in accordance with an example implementation of the present disclosure.
Figure 8:
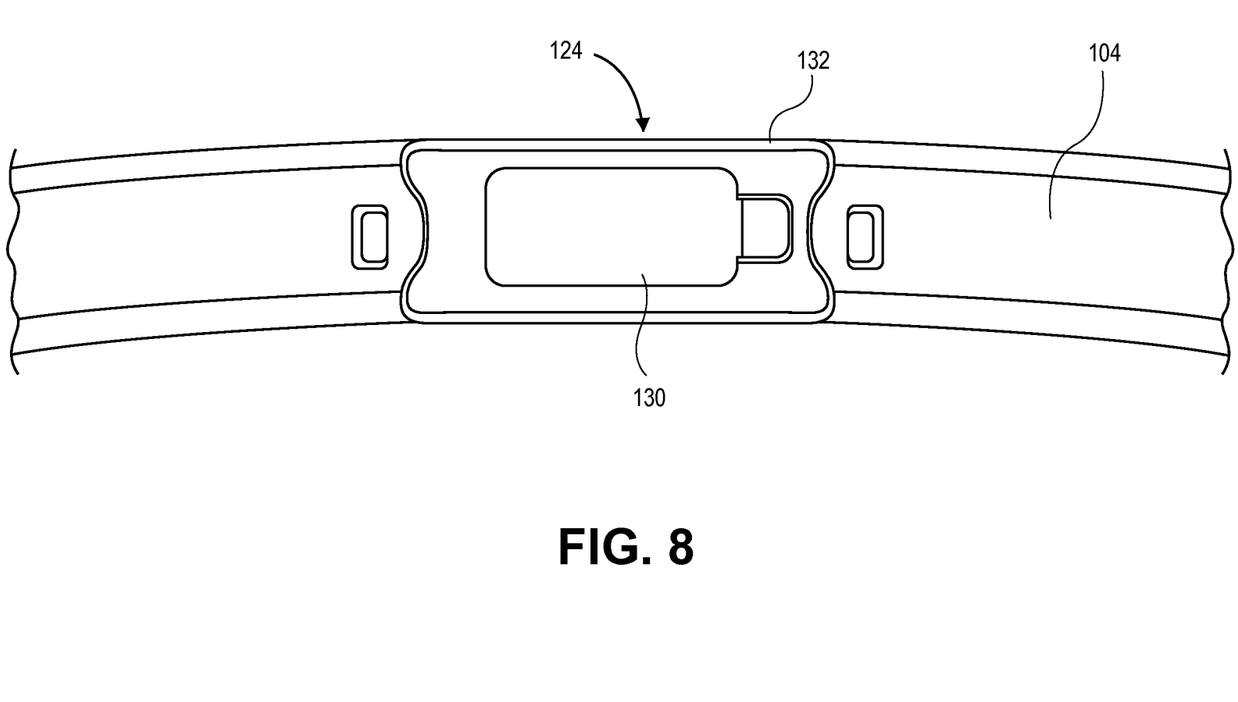
FIG. 8 is a bottom plan view illustrating the unitary wristband of the fitness monitor shown in FIG. 1, in accordance with an example implementation of the present disclosure.

As shown in FIGS. 3 and 7, the housing receiving structure 124 defines an upper opening 130 shaped such that a display 106 associated with a housing 102 may be visible through the opening 130 when the housing 102 is substantially secured within the housing receiving structure 124. The upper opening 130 may expose the display 106, which is associated with the housing 102, or include a clear cover (e.g., plastic protective shield) which protects the display 106. The housing receiving structure 124 may also define one or more side openings 132 shaped such that a side surface of the housing 102 may be visible through one or more sides of the housing receiving structure 124. FIGS. 7 and 8 depict an example wristband 104 without a corresponding housing 102 secured within a housing receiving structure 124 to more clearly illustrate the upper and side openings 130, 132.

In implementations, the housing 102 of the module 101 may be removably coupled with the wristband 104. For example, the housing 102 may be inserted into the housing receiving structure 124 such that the housing 102 and wristband 104 are secured together to form a wrist-worn fitness monitor 100. Likewise, in implementations, the wristband 104 and the housing 102 may be separated by applying force to release the housing 102 from the wristband 104. Separation of the wristband 104 and the housing 102 enables users to quickly replace either component. Users may desire to replace the wristband 104 for aesthetic purposes (e.g., to change to a wristband having a different color) or to replace the wristband 104 when it is worn or damaged. The module 101 may be removed and replaced in a similar manner (e.g., for similar reasons).

Implementations of the present disclosure provide a fitness monitor 100 having reduced thickness and width. Reduced thickness and width dimensions are beneficial for users interested in using wrist-worn fitness monitors having minimal form factor. Unlike conventional wrist-worn watches and devices, as shown in FIG. 6, the fitness monitor 100 thickness is determined by the height of the upper portion 126 (including a lens 135 disposed over the display 106) and the height of the lower portion 128 of the housing 102. In embodiments, the dimensions of the upper portion 126 and the lower portion 128 are defined by the height of components stacked within the housing 102 (e.g., the display 106, integrated circuit devices, the batteries 118, etc.). Similarly, the width of the fitness monitor 100 is determined by the width of components in the housing 102 (e.g., the diameter of the one or more circular batteries 118, the lateral structures to enclose the housing 102 within the housing receiving structure 124, etc.).

In implementations, the thickness and width of the fitness monitor 100 is at least substantially the same as the thickness and width of the housing 102 (e.g., the thickness and width are the same or not appreciably larger or smaller as perceived by an average user) because the housing 102 is substantially enclosed in the housing receiving structure 124 (e.g., the wristband 104 does not add thickness or width to the housing 102 of the fitness monitor 100). Reduction in the thickness and width of the housing 102 may result in a proportional reduction in the thickness and width of the fitness monitor 100.

A variety of techniques may be used to interface a first element of a fitness monitor, such as a housing 102, with a second element of the fitness monitor, such as a housing receiving structure 124. For instance, in implementations, the housing 102 may be interlocked with, associated with, coupled with, attached to, fastened to, connected to, joined to or secured to the housing receiving structure 124. In the embodiment shown in FIG. 5, the wristband 104 may include one or more protrusions along the opening (e.g., within the housing receiving structure 124) where the housing 102 of the module 101 is positioned when the housing 102 is interfaced with the housing receiving structure 124 of the wristband 104. In implementations, a protrusion may be a continuous ridge (e.g., a channel) or stand-alone tab that couples or interlocks with a recess in the housing 102 when positioned to be in alignment. For example, a continuous ridge may couple with a continuous channel (or groove) and a stand-alone tab may couple with a slot when the housing 102 and the housing receiving structure 124 are aligned. As shown in FIG. 5, implementations of the present disclosure include a wristband 104 having four continuous protrusions 134A, 134B, 134C, 134D defined within the housing receiving structure 124 in which a housing 102 with four continuous recesses 136A, 136B, 136C, 136D is to be received (the protrusions and recesses will interlock when positioned to align).

As shown above, the housing receiving structure 124 may include continuous protrusions 134A, 134B extending into the vertical plane and continuous protrusions 134C, 134D extending into the lateral plane. The continuous recessed areas 136A, 136B, 136C, 136D of the housing 102 may be present in the vertical and laterals planes as well to enable the protrusions 134A, 134B, 134C, 134D and corresponding recesses 136A, 136B, 136C, 136D to interlock when aligned. Interlocking refers to a respective protrusion occupying the space created by a respective recess when the respective protrusion and recess are aligned. For example, the wristband protrusions 134C, 134D in the lateral plane may interlock with a housing recess in the lateral plane 136C, 136D and the wristband protrusions 134A, 134B may interlock with a housing recess 136A, 136B in the vertical plane. The vertical and lateral planes may be defined with respect to a plane defined by a surface 133 of the display 106. For example, the vertical protrusions 134A, 134B and the vertical recesses 136A, 136B may be defined in a plane that is generally orthogonal to the plane defined by the surface 133 of the display 106; and the horizontal protrusions 134C, 134D and the horizontal recesses 136C, 136D may be defined in a plane that is generally parallel to the plane defined by the surface 133 of the display 106.

This configuration provides restriction in the vertical and lateral directions when the continuous recessed areas 136A, 136B, 136C, 136D of the housing 102 are aligned with the continuous protrusions 134A, 134B, 134C, 134D of the housing receiving structure 124 within the wristband 104. The wristband protrusions 134C, 134D in the lateral plane serve to limit up and down movements of the housing 102 when interlocked with respective housing recesses 136C, 136D in the lateral plane. Similarly, the wristband protrusions 134A, 134B in the vertical plane serve to limit lateral (e.g., side-to-side) movements of the housing 102 when interlocked with respective housing recesses 136A, 136B in the vertical plane.

In implementations, the housing 102 and the housing receiving structure 124 within the wristband 104 may be composed of a flexible material (e.g., a rubber and plastic blend) enabling the housing 102 to be decoupled (or detached) from the housing receiving structure 124 of the wristband 104 when a vertical and/or lateral force exceeding the resistance to movement, which is created by the above-described interlocking, is applied to the housing 102 and/or the wristband 104.

In implementations, the housing 102 may include upper and lower portions 126, 128 having a shape such that a recess is formed when the upper portion and lower portion 126, 128 of the housing 102 are aligned. As shown in FIG. 5, the lower portion 128 of the housing 102 may extend wider than the upper portion 126 and include a vertical portion such that recesses are formed in the vertical plane 136A, 136B when the upper and lower portions 126, 128 of the housing 102 are aligned. The protrusions 134A, 134B of the housing receiving structure 124 may interlock with housing recesses 136A, 136B in the vertical plane when the housing receiving structure 124 and the housing 102 are aligned.

The upper portion 126 of the housing 102 may be shaped to include recesses 136C, 136D in the lateral plane. The protrusions 134C, 134D of the housing receiving structure 124 may interlock with housing recesses 136C, 136D in the lateral plane when the housing receiving structure 124 and the housing 102 are aligned.

As shown in FIG. 5, an outer surface of the housing receiving structure 124 defines a generally curvilinear surface 138. In one or more implementations of the present disclosure, the curvilinear surface 138 partially extends between a respective vertical protrusion 134A, 134B and a corresponding lateral protrusion 134C, 134D.

It is to be understood that various combinations of protrusions and recesses are possible. For example, the housing 102 may include protrusions and the housing receiving structure 124 of the wristband 104 may include recesses that interlock when aligned. It may be possible to for the housing 102 and the wristband 104 to each include a protrusions and recesses that interlock when aligned.

CONCLUSION

Although techniques to couple a module comprising a housing and a wristband comprising a housing receiving structure configured to receive the housing have been described in language specific to structural features and/or methodological acts, it is to be understood that the appended claims are not necessarily limited to the specific features or acts described. Rather, the specific features and acts are disclosed as exemplary forms of implementing the claimed devices and techniques.

What is claimed is:

1. A fitness monitor comprising:
   a module comprising a housing including two side surfaces, the housing having a first thickness; and
   a unitary wristband configured to be worn about a wrist of a user, the unitary wristband comprising a housing receiving structure configured to receive the housing and shaped to secure a first portion of each side surface within the housing receiving structure, the combination of the housing receiving structure and the housing having a second thickness,
   wherein a second portion of each side surface not secured within the housing receiving structure is exposed; and
   wherein the second thickness is equal to the first thickness.

2. The fitness monitor as recited in claim 1, wherein the housing has a first width and the combination of the housing receiving structure and the housing has a second width, wherein the second width is equal to the first width.

3. The fitness monitor as recited in claim 1, wherein the housing defines a plurality of recesses, and wherein the housing receiving structure comprises a plurality of protrusions, respective ones of the protrusions configured to interlock with a respective recess to limit movement of the housing when the housing is interfaced with the housing receiving structure.

4. The fitness monitor as recited in claim 3, wherein the plurality of protrusions comprise at least one lateral protrusion and at least one vertical protrusion, and wherein the plurality of recesses comprise at least one lateral recess and at least one vertical recess, the at least one lateral protrusion configured to interlock with the at least one lateral recess when aligned and the at least one vertical protrusion configured to interlock with the at least one vertical recess when aligned.

5. The fitness monitor as recited in claim 4, wherein an outer surface of the housing receiving structure defines a generally curvilinear surface defined with respect to a cross-sectional profile of the housing receiving structure, the generally curvilinear surface extending between a lateral protrusion and a vertical protrusion.

6. The fitness monitor as recited in claim 1, wherein the housing comprises an upper portion and a lower portion, the lower portion configured to be proximal to the wrist of the user and the upper portion configured to be distal to the wrist of the user when the fitness monitor is worn about the wrist of a user, the upper portion having an upper portion height and the lower portion having a lower portion height, wherein the first thickness is equal to the height of the upper portion height and the lower portion height.

7. The fitness monitor as recited in claim 1, wherein the module comprises an electronic module, the electronic module including:
   a motion sensor configured to sense motion and generate motion data based upon the sensed motion;
   a memory, the memory configured to store the motion data sensed by the motion sensor; and
   a processor coupled to the memory device, the processor configured to determine activity data based upon the motion data stored in the memory.

8. The fitness monitor as recited in claim 1, wherein the electronic module includes a display configured to present information associated with an activity data associated with a user, the display including a lens that is at least substantially coplanar with a surface of the housing receiving structure when the housing of the module is received in the housing receiving structure.

9. The fitness monitor as recited in claim 4, wherein the vertical recess defined by the housing is a continuous vertical recess formed within the side surface of the housing.

10. The fitness monitor as recited in claim 9, wherein the vertical recess is formed along locations where the first portion of the side surface secured within the housing receiving structure contacts the second portion of the side surface.

11. The fitness monitor as recited in claim 6, wherein the upper portion of the housing includes the first portion of each side surface and the lower portion of the housing includes the second portion of each side surface.

12. A wristband for a fitness monitor, the wristband comprising:
   a unitary wristband configured to receive an electronics module having a housing including two side surfaces and having a first width and a first thickness, the unitary wristband including:
      a housing receiving structure configured to receive the housing and shaped to secure a first portion of each side surface within the housing receiving structure, the combination of the housing receiving structure and the housing having a second width and a second thickness,
      wherein a second portion of each side surface not secured within the housing receiving structure is exposed; and
      wherein the second width is equal to the first width and the second thickness is equal to the first thickness.

13. The wristband as recited in claim 12, wherein the housing receiving structure includes a plurality of protrusions and the housing defining a plurality of recesses, and wherein each protrusion is configured to interlock with a respective recess to limit movement of the housing when the housing is interfaced with the housing receiving structure.

14. The wristband as recited in claim 13, wherein the plurality of protrusions comprise at least one lateral protrusion and at least one vertical protrusion, wherein the plurality of recesses comprise at least one lateral recess and at least one vertical recess, the at least one lateral protrusion configured to interlock with the at least one lateral recess when aligned and the at least one vertical protrusion configured to interlock with the at least one vertical recess when aligned.

15. The wristband as recited in claim 14, wherein an outer surface of the housing receiving structure defines a generally curvilinear surface defined with respect to a cross-sectional profile of the housing receiving structure, the generally curvilinear surface extending between a lateral protrusion and a vertical protrusion.

16. The wristband as recited in claim 13, wherein the housing comprises an electronic module configured to track activity data associated with a user.

17. The wristband as recited in claim 16, wherein the electronic module includes a display configured to present information associated with the activity data, the display including a lens that is at least substantially coplanar with a surface of the housing receiving structure.

18. A fitness monitor comprising:
a module comprising a housing including two side surfaces, the housing having a first thickness; and
a unitary wristband including a housing receiving structure configured to receive the housing and shaped to secure a first portion of each side surface within the housing receiving structure, the combination of the housing receiving structure and the housing having a second thickness, the housing receiving structure including a plurality of protrusions and the housing defining a plurality of recesses, each protrusion is configured to interlock with a respective recess to limit movement of the housing when the housing is interfaced with the housing receiving structure,
wherein a second portion of each side surface not secured within the housing receiving structure is exposed; and
wherein the second thickness is equal to the first thickness.

19. The fitness monitor as recited in claim 18, wherein the housing has a first width and the combination of the housing receiving structure and the housing has a second width, wherein the second width is equal to the first width.

20. The fitness monitor as recited in claim 18, wherein the plurality of protrusions comprise at least one lateral protrusion and at least one vertical protrusion and wherein the plurality of recesses comprise at least one lateral recess and at least one vertical recess, the at least one lateral protrusion configured to interlock with the at least one lateral recess when aligned and the at least one vertical protrusion configured to interlock with the at least one vertical recess when aligned.

21. The fitness monitor as recited in claim 18, wherein the housing comprises an upper portion and a lower portion, the lower portion configured to be proximal to the wrist of the user and the upper portion configured to be distal to the wrist of the user when the fitness monitor is worn about the wrist of a user, the upper portion having an upper portion height and the lower portion having a lower portion height, wherein the first thickness is equal to the height of the upper portion height and the lower portion height.

22. The fitness monitor as recited in claim 18, wherein an outer surface of the housing receiving structure defines a generally curvilinear surface defined with respect to a cross-sectional profile of the housing receiving structure, the generally curvilinear surface extending between a lateral protrusion and a vertical protrusion.

23. The fitness monitor as recited in claim 18, wherein the module comprises an electronic module, the electronic module including:
a motion sensor configured to sense motion and generate motion data based upon the sensed motion;
a memory device coupled to the motion sensor, the memory device configured to store the motion data;
a processor coupled to the memory device, the processor configured to determine activity data based upon the motion data; and
a display configured to present information associated with the activity data, the display including a lens that is at least substantially coplanar with a surface of the housing receiving structure.

* * * * *